United States Patent [19]

Hamilton

[11] Patent Number: 5,364,876

[45] Date of Patent: Nov. 15, 1994

[54] OMEGA-[2-(ALKYL)PHENYL]-2-AMINOALKANOIC ACIDS AS ANTAGONISTS OF EXCITATORY AMINO ACID RECEPTORS

[75] Inventor: Gregory S. Hamilton, Catonsville, Md.

[73] Assignee: Guilford Pharmaceuticals Inc., Baltimore, Md.

[21] Appl. No.: 984,452

[22] Filed: Dec. 2, 1992

[51] Int. Cl.$^5$ .................. C07D 257/04; A61K 31/10; A61K 31/195; A61K 31/215

[52] U.S. Cl. ........................... 514/381; 514/538; 514/562; 514/567; 548/253; 560/12; 560/38; 562/433; 562/41

[58] Field of Search ............ 548/253; 514/381, 538, 514/562, 567; 560/12, 38; 562/41, 433

[56] References Cited

U.S. PATENT DOCUMENTS

| | | | |
|---|---|---|---|
| 4,657,899 | 4/1987 | Rzeszotarski et al. | 514/120 |
| 4,761,405 | 8/1988 | Rzeszotarski et al. | 514/114 |
| 4,822,780 | 4/1989 | Tsuda et al. | 514/119 |
| 4,918,064 | 4/1990 | Cordi et al. | 514/114 |
| 5,049,555 | 9/1991 | Rzeszotarski et al. | 514/114 |

FOREIGN PATENT DOCUMENTS 432994  6/1991  European Pat. Off. .

OTHER PUBLICATIONS

Watkins et al., "Excitatory Amino Acid Transmitters," *Amer. Rev. Pharmacol. Toxicol.* (1981), vol. 21 pp. 165-204.

Schwarcz et al., "Quinolinic Acid: An Endogenous Metabolite that Produces Axon-Sparing Lesions in Rat Brain," *Science,* Jan. 1983, vol. 219, pp. 316-318.

Simon et al., "Blockade of N-Methyl-D-Aspartate Receptors May Protect Against Ischemic Damage in the Brain," *Science,* vol. 226, pp. 850-852, (1984).

*Primary Examiner*—David B. Springer
*Attorney, Agent, or Firm*—Nath, Amberly & Associates

[57] ABSTRACT

The present invention pertains to antagonists of excitatory amino acid receptors, their method of preparation as well as compositions pertaining to them, which have the general formula:

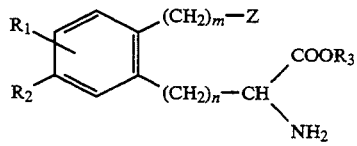

wherein m and n are independently 0,1,2, or 3: R1 and R2 are selected from the group consisting of hydrogen, halogen, halomethyl, nitro, amino, alkoxy, hydroxyl, hydroxymethyl, C1 to C6 lower alkyl, C7 to C12 higher alkyl, aryl and aralkyl; Z is a monoacidic radical; R3 is selected from the group consisting of hydrogen, and C1 to C6 lower alkyl; the stereoisomers thereof in their resolved or racemic form, and pharmaceutically acceptable salts thereof. In a preferred embodiment m is 2 or 3 and n is 1.

21 Claims, No Drawings

OMEGA-[2-(ALKYL)PHENYL]-2-AMINOALKANOIC ACIDS AS ANTAGONISTS OF EXCITATORY AMINO ACID RECEPTORS

BACKGROUND OF THE INVENTION

1. Field of the Invention

The present invention pertains to novel non-N-methyl-D-aspartic acid excitatory amino acid (EAA) antagonists and particularly to novel, potent and selective antagonists of kainic acid (KA) and AMPA-type [(RS)-alpha-aminomethyl-3-hydroxy-5-methylisoxazole propionic acid]-type receptors having anxiolytic, anticonvulsant, antiepileptic, analgesic, antiemetic, neuroprotective and cognition enhancing actions achieved through the antagonisms of these receptors. In particular, the invention is directed to: 2-[(alkyl)phenyl]-2-aminoalkanoic acids and their interaction with KA and AMPA receptors, their pharmaceutically acceptable salts, and to uses thereof.

2. Description of the Prior Art

Excitatory amino acids (EAA) mediate a substantial portion of the chemical synaptic activity occurring in the central nervous system. Current understanding recognizes at least three major ionotropic receptors for EAAs. Most commonly identified by prototypical agonists, these include:

(1) receptors activated by AMPA [(RS)-alpha-aminomethyl-3-hydroxy-5-methylisoxazole propionic acid], a cyclic analog of L-glutamate (GLU), (2) receptors recognizing the pyrrolidine neurotoxin kainic acid (KA), and (3) receptors responding to N-methyl-D-aspartate (NMDA), a synthetic analog of L-aspartate (D. R. Curtis, A. W. Duggar, D. Felix, G. A. R. Johnston, A. K. Tebecis and J. C. Watkins, Brain Res., 41, 283–301 (1972); J. C. Watkins and R. H. Evans., Ann. Rev. Pharmacol. Toxicol., 21, 165–204 (1981); A. C. Foster and G. Fagg, Brain Res. Rev. 7, 103–164 (1984)]. In addition to these major channel-linked receptors, evidence now suggests the presence of "metabotropic" EAA receptors which directly activate second messenger responses (D. Schoepp, J. Bockaert and F. Sladeczek, In C. Lodge and G. L. Collingridge (eds.) Tr. Pharmacol. Sci., Special Report, "The Pharmacology of Excitatory Amino Acids," Elsevier, Cambridge, UK., pages 74–81, (1991)]. Furthermore, it is now apparent that the NMDA-mediated ionotropic responses are subject to complex regulatory influences and, that this particular recognition site may exist as a supramolecular entity similar to the GABA/benxodiazepine/barbiturate effector proteins [E. Costa, Neuropsychopharmacology, 2, pages 167–174 (1989)].

In general, EAA agonists are potent convulsants in animal models. Additionally, AMPA, KA and the endogenous NMDA agonist, quinolinic acid (QUIN) and the mixed ionotropic/metabotropic agonist ibotenic acid have been used to produce laboratory models of neurodegenerative disorders [K. Biziere, J. T. Slevin, R. Zaczek, J. S. Collins and J. T. Coyle. IN H. Yoshida, Y. Hagihara and S. Ebashi (eds.), "Advances in Pharmacology and Therapeutics," Pergamon, New York, 1982, pp. 271–276; R. Schwarcz, W. O. Whetsell and R. M. Mango, Science, 219, pages 316–318 (1983)]. It has been suggested for some time that a dysfunction in EAA neurotransmission may contribute to the neuropathology associated with epilepsies and neurodegenerative conditions [B. Meldrum and M. Williams (eds.), "Current and Future Trends in Anticonvulsant, Anxiety and Stroke Therapy," Wiley Liss, New York, (1990)].

The development of selective NMDA antagonists has further expanded the understanding of EAA neurotransmission, physiology and pathophysiology in the mammalian brain. In particular, substantial preclinical evidence is now available suggesting that NMDA receptor antagonists may be useful as anxiolytics, anticonvulsants, antiemetics [European Patent Application No. 432,994], antipsychotics or muscle relaxants, and that these compounds may prevent or reduce neuronal damage in instances of cerebral ischemia, hypoxia, hypoglycemia or trauma [R. P. Simon, J. H. Swan, T. Griffiths and B. S. Meldrum, Science, 226, pages 850–852 (1984); D. N. Stephens, B. S. Meldrum, R. Weidman, C. Schneider and M. Grutzner, Psychopharmacology, 90, pages 166–169 (1986); D. Lodge and G. L. Collingridge (eds.) "The Pharmacology of Excitatory Amino Acids," Elsevier Trends Journals, Cambridge, UK. (1991); A. I. Fader, J. A. Ellison and L. J. Noble, Eur. J. Pharmacol., 175, pages 165–174 (1990)].

Given the broad therapeutic potential of EAA antagonists, it is not surprising that efforts have been initiated to identify additional antagonist compounds. The advent of potent and selective antagonists of EAAs exemplified by $\alpha$-amino-$\omega$-phosphonoalkylcarboxylic acids has provided a point of departure for the pharmacologic intervention of EAA action at their receptors [J. C. Watkins, Can. J. Physiology Pharmacol., 69, 1064–1075 (1991)]. While there has been substantial success in finding competitive and non-competitive antagonists of NMDA receptors, there are few reports of potent and selective antagonists of KA or AMPA-type EAA receptors [J. C. Watkins, P. Krogsgaard-Larsen and T. Honore, In D. Lodge and G. L. Collingridge (eds.), "The Pharmacology of Excitatory Amino Acids," Elseiver Trends Journals, Cambridge, UK., pages 4–12 (1991); M. J. Sheardown, E. O. Nielsen, J. A. Hansen, P. Jacobsen and T. Honore, Science, 247, pages 571–573 (1990); A. Frasden, J. Drejer and A. Shousboe, J. Neurochem., 53, pages 297–300 (1989)]. Identification of such antagonists is important since these agents are expected to share many of the potential therapeutic actions of antagonists of NMDA-type EAA receptors.

In the past, 2-amino-4-(2-phosphonomethylphenyl)-butyric acid has been reported by Matoba et al. [Chem. Pharm. Bull. 32, pages 3918–3925 (1984)]. More particularly, Matoba et al. prepared several amino-phosphonic acids and notably, 2-amino-5-phosphonopentanoic acid, 2-amino-4-(2-amino-5-phosphonomethyl-phenyl)-butyric acid, 2-(2-amino-2-carboxy) ethylphenyl-phosphonic acid and N-benzylproline-4-phosphonic acid. One of the target compounds, 2-amino-4-(2-phosphonomethylphenyl)butyric acid was synthesized starting with (2-bromoethyl) phenethylbromide. This dibromide was treated with triethyl phosphite to give diethyl (2-(2-bromoethylphenyl)methylphosphonate, and this bromophosphonate derivative was treated with sodium diethyl acetamindomalonate to give the expected acetamidomalonylphosphonate derivative which was purified through a silica gel column. It should be pointed out that none of the Matobe et al. compounds contain substituents on the benzene ring.

Related compounds having NMDA antagonist activity has been reported in Rzeszotarski et al., U.S. Pat. No. 4,657,899. In particular, Rzeszotarski et al. disclose potent and selective EAA neurotransmitter receptor antagonists having the general formula:

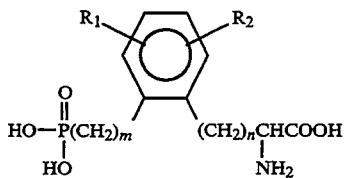

wherein $R_1$ and $R_2$ are the same or different and are selected from the group consisting of hydrogen, lower alkyl, halogen, amino, nitro, trifluoromethyl or cyano, or taken together are —CH=CH—CH=CH—; n and m=0, 1, 2, or 3; and the pharmaceutically acceptable salts and the 2-acetamido-2-carboethoxy esters thereof. Rzeszotarski et al. also disclose specific compounds, including 2-amino-3-[2-(2-phosphonoethyl)phenyl]-propanoic acid, 2-amino-3-[2-(3-phosphonopropyl)-phenyl]propanoic acid, 2-amino-5-[2-phosphonomethylphenyl]pentanoic acid, and 2-amino-3-[2-phosphonomethylphenyl]propanoic acid which are disclosed as antagonists of NMDA and show very low binding affinity for kainate receptors; see Table I on column 13 of U.S. Pat. No. 4,657,899. The valuable pharmacological properties of the present new compounds are particularly surprising in view of the compounds disclosed and described in U.S. Pat. No. 4,657,899.

SUMMARY OF THE INVENTION

The present invention provides an excitatory amino acid KA/AMPA receptor antagonist compounds having the general formula:

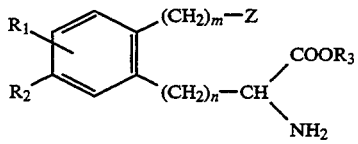

wherein n and m are independently 0, 1, 2, or 3; $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ $C_{12}$ higher alkyl, aryl, and aralkyl; Z is a monoacidic radical, such as carboxyl, sulfonyl or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment, m is 2 or 3 and n is 1.

In one embodiment the invention provides a potent, selective excitatory amino acid KA/AMPA receptor antagonist compound having the general formula:

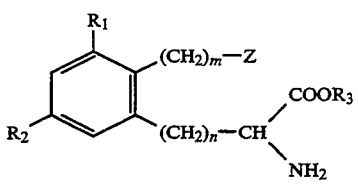

wherein m and n are independently 0, 1, 2, or 3: $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl, and aralkyl; Z is a monoacidic radical, such as carboxyl, sulfonyl, or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment m is 2 or 3 and n is 1.

In addition, the invention provides a potent and selective KA/AMPA receptor antagonist having the general formula:

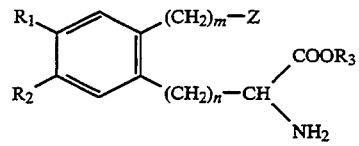

wherein m and n are independently 0, 1, 2, or 3: $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl, and aralkyl; Z is a monoacidic radical, such as carboxyl, sulfonyl or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment m is 2 or 3 and n is 1.

In another preferred embodiment, when $R_1$ or $R_2$ are hydrogen, the other is not hydrogen.

Another aspect of the invention involves use of the pharmaceutical compositions for relieving pain, treatment of convulsions or epilepsy, enhancing cognition, treating psychosis, preventing neurodegeneration, treating cerebral ischemic or trauma-induced damage, and treating emesis.

A further aspect of the invention involves a method for antagonizing excitatoryamino acid kainic acid or AMPA receptors by utilizing a compound having the general formula:

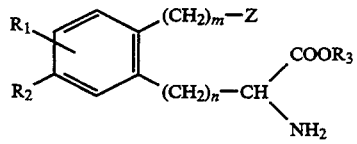

wherein n and m independently are 0, 1, 2, or 3; $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl, and aralkyl; Z is a monoacidic radical, such as carboxyl, sulfonyl or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment of this method m is 2 or 3 and n is 1.

Preferred compounds according to the invention include:
5-methyl-2-(3-carboxypropyl)phenylalanine
5-methyl-2-(3-sulfonoethyl)phenylalanine
5-methyl-2-(3-carboxyethyl)phenylalanine 5-methyl-2-(2'-tetrazolylethyl)phenylalanine
3,5-dimethyl-2-(2-carboxypropyl)phenylalanine
3,5-dimethyl-2-(2-sulfonoethyl)phenylalanine
3,5-dimethyl-2-(2-carboxyethyl)phenylalanine
3,5-dimethyl-2-(2'-tetrazolylethyl)phenylalanine
5-chloro-2-(2-carboxypropyl)phenylalanine
5-chloro-2-(2-sulfonoethyl)phenylalanine
5-chloro-2-(2-carboxyethyl)phenylalanine
5-chloro-2-(2'-tetrazolylethyl)phenylalanine
5-methyl-(2-carboxypropyl)phenylalanine
5-methyl-(2-sulfonoethyl)phenylalanine
5-methyl-(2-carboxyethyl)phenylalanine
5-methyl-(2'-tetrazolylethyl)phenylalanine
5-fluoro-2-(2-carboxypropyl)phenylalanine
5-fluoro-2-(2-sulfonoethyl)phenylalanine
5-fluoro-2-(2-carboxyethyl)phenylalanine
5-fluoro-2-(2'-tetrazolylethyl)phenylalanine
4,5-dichloro-2-(2-carboxypropyl)phenylalanine
4,5-dichloro-2-(2-sulfonoethyl)phenylalanine
4,5-dichloro-2-(2-carboxyethyl)phenylalanine
4,5-dichloro-2-(2'-tetrazolylethyl)phenylalanine

DETAILED DESCRIPTION OF THE INVENTION

The structure and formulation of the novel compounds of the invention was the result of an extensive research effort into the antagonism of excitatory amino acid (EAA) neurotransmission with focus on the kainic acid (KA) and AMPA subtypes of EAA receptor.

It is generally accepted that L-glutamic acid (GLU) is the principal excitatory neurotransmitter in the vertebrate central nervous system (CNS). Ion channel-linked or "ionotropic" EAA receptor subtypes include those selectively activated by N-methyl-D-aspartate (NMDA), alpha-amino-3-hydroxy-5-methyl-4-isoxazole propionic acid (AMPA), and kainic acid (KA). A "metabotropic" GLU receptor 4-isoxazole propionic acid (AMPA), and kainic acid (KA). A "metabotropic" GLU receptor coupled to phospholipid metabolism and a putative GLU autoreceptor have also been identified. L-glutamic acid is also believed to have an important physiological role in the functioning of the CNS since a great majority of CNS neurons utilize GLU as their neurotransmitter.

Beyond its involvement in excitatory neurotransmission, GLU has been suggested to play a role in CNS pathologies characterized by heightened neuronal activity or sensitivity, including epilepsy, ischemic or trauma-induced neuronal damage, and certain neurologic and neurodegenerative disorders. Accordingly, the pharmacological manipulation of GLU receptors is therapeutically useful in the treatment of several CNS disorders and diseases.

The NMDA receptor is the most well-characterized of the GLU receptor subtypes because of the availability of potent and selective antagonists. D-(—)-2-amino-5-phosphonopentanoic acid (AP5) and D-(—)-2-amino-5-phosphonoheptanoic acid (AP7) were among the first NMDA antagonists identified and act competitively by binding to the GLU recognition site.

Competitive NMDA antagonists have been demonstrated to possess therapeutic potential as anticonvulsant and cerebroprotective agents. However, a growing body of evidence suggests that blockade of non-NMDA receptors might also be useful in the treatment of CNS disorder involving glutamatergic neurotransmission. In support of this hypothesis, KA-induced seizures have been used as animal models of temporal lobe epilepsy in humans, suggesting that KA antagonists might be a useful therapeutic tool for the management of this disorder. Another potential therapeutic use for a KA and/or AMPA antagonist in the treatment of neurodegenerative disorders is indicated by the finding that intrastriatal administration of KA produces a pattern of neuronal damage in rats similar to that observed in Huntington's chorea. Non-NMDA receptors have also been implicated in neurologic disorders including Lathyrism, an upper motor neuron disease characterized by spastic paraparesis, and Guam's disease, a form of amyotrophic lateral sclerosis.

In contrast to NMDA receptors, a limited number of KA/AMPA receptor antagonists have been described, the majority of which are weak and relatively non-selective; for this reason, the full characterization of the functional and physiological properties of these receptors has not been realized to date.

The compounds of the present invention have been identified which competitively antagonize KA and AMPA-induced currents in Xenopus oocytes injected with rat brain mRNA. Members of these compounds have also been shown to possess anticonvulsant properties and to protect against KA-induced striatal toxicity in vivo. These compounds do not interact appreciably with the high affinity [$^3$H] KA binding sites in rat brain membranes. While the reason for this latter finding is not known, there is considerable controversy regarding the functional relevance of high affinity [$^3$H] KA binding sites since much higher concentrations of KA are required to produce in vitro responses.

The structure and formulation of the novel compounds of this invention relate specifically to EAA receptors activated by either KA or AMPA for which only a limited number of quinoxalines have been identified as specific antagonists. The valuable pharmacological properties of the present new compounds are particularly surprising in view of the known relationship between EAA receptor antagonist activity and the nature of the omega-acidic moiety as it pertains to NMDA receptor binding.

In a preferred embodiment, the novel compounds of the present invention provide potent antagonists having greater affinity for KA and AMPA receptors and lesser or no affinity for other CNS receptors, rendering the compounds very selective. This would permit one to selectively antagonize one EAA receptor in tissues also containing other EAA receptors. Fewer side effects can be expected as a result of the greater affinity and selectivity of the compounds of the present invention.

Compounds of the present invention have the formula:

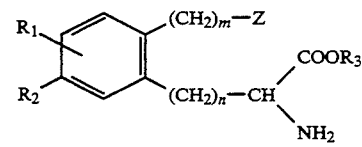

wherein m and n are independently 0, 1, 2, or 3: $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl, and aralkyl; Z is a monoacidic radical; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment m is 2 or 3 and n is 1.

A particularly preferred form of the compounds of the present invention has the formula:

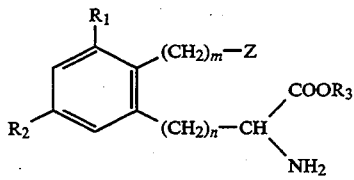

wherein m and n are independently 0, 1, 2, or 3: $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl, and aralkyl; Z is a monoacidic radical, such as carboxyl, sulfonyl or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment m is 2 or 3 and n is 1.

In addition, the invention provides a potent and selective KA/AMPA receptor antagonist having the general formula:

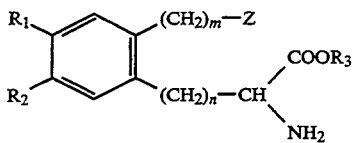

wherein m and n are independently 0, 1, 2, or 3: $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl; Z is a monoacidic radical, such as carboxyl, sulfonyl or tetrazolyl; $R_3$ is selected from the group consisting of hydrogen, and $C_1$ to $C_6$ lower alkyl; the stereoisomers thereof in their resolved or racemic form, and pharmaceutically acceptable salts thereof. In a preferred embodiment m is 2 or 3 and n is 1.

As used in the specification and claims, "alkyl" is a paraffinic hydrocarbon group which may be derived from an alkane by dropping one hydrogen from the formula, such as methyl, ethyl, propyl, isopropyl, butyl, and so forth.

"Halogen" includes bromo, fluoro, chloro and iodo; "halomethyl" includes mono-, di-, and tri- halo groups including trifluoromethyl; amino compounds include amine ($NH_2$) as well as substituted amino groups comprising alkyls of one through six carbons; "aryl" is an aromatic ring compound such as benzene, phenyl, napthyl and substituted forms thereof; "aralkyl" is an aryl connected through an alkyl chain, straight or branched, of from one through six carbons.

Preferred compounds of the present invention include:

5-methyl-2-(3-carboxypropyl)phenylalanine
5-methyl-2-(3-sulfonoethyl)phenylalanine
5-methyl-2-(3-carboxyethyl)phenylalanine
5-methyl-2-(2'-tetrazolylethyl)phenylalanine
3,5-dimethyl-2-(2-carboxypropyl)phenylalanine
3,5-dimethyl-2-(2-sulfonoethyl)phenylalanine
3,5-dimethyl-2-(2-carboxyethyl)phenylalanine
3,5-dimethyl-2-(2'-tetrazolylethyl)phenylalanine
5-chloro-2-(2-carboxypropyl)phenylalanine
5-chloro-2-(2-sulfonoethyl)phenylalanine
5-chloro-2-(2-carboxyethyl)phenylalanine
5-chloro-2-(2'-tetrazolylethyl)phenylalanine
5-methyl-(2-carboxypropyl)phenylalanine
5-methyl-(2-sulfonoethyl)phenylalanine
5-methyl-(2-carboxyethyl)phenylalanine
5-methyl-(2'-tetrazolylethyl)phenylalanine
5-fluoro-2-(2-carboxypropyl)phenylalanine
5-fluoro-2-(2-sulfonoethyl)phenylalanine
5-fluoro-2-(2-carboxyethyl)phenylalanine
5-fluoro-2-(2,-tetrazolylethyl)phenylalanine
4,5-dichloro-2-(2-carboxypropyl)phenylalanine
4,5-dichloro-2-(2-sulfonoethyl)phenylalanine
4,5-dichloro-2-(2-carboxyethyl)phenylalanine
4,5-dichloro-2-(2'-tetrazolylethyl)phenylalanine The preparation of the compounds for administration in pharmaceutical preparations may be accomplished in a variety of methods well known to those skilled in the art of synthetic organic chemistry. Appropriate pharmaceutically acceptable salts within the scope of the invention include those derived from mineral acids such as hydrochloric acid, phosphoric acid, hydrobromic acid and sulfuric acid, as well as organic acids such as tartaric acid, methanesulfonic acid, benzenesulfonic acid, p-toluenesulfonic acid, and the like, giving respectively the hydrochloride, phosphate, hydrobromide, sulfate, tartrate, methanesulfonate, benzenesulfonate, p-toluenesulfonate, and the like, or those derived from bases such as suitable organic and inorganic bases. Examples of suitable inorganic bases for the formulation of salts of the compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the preparation of pharmaceutically acceptable base addition salts with compounds of the present invention include organic bases which are nontoxic and strong enough to form such salts. These organic bases form a class whose limits are clearly understood by those skilled in the art. Merely for the purposes of illustration, the class may be said to include mono-, di-, and trialkylamines, such as methylamine, dimethylamine and triethylamine; mono-, di-, and trihydroxylalkylamines such as mono-, di-, and triethanolamine; amino acids such as arginine and lysine; guanidine; N-methyl-D-glucosamine; N-methylglucamine; L-glutamine; N-methylpiperazine; morpholone; ethylenediamine; N-benzylphenethylamine; tris(trihydroxymethyl)aminomethane; and the like.

The compounds of the invention contain an asymmetric carbon atom. Thus, the invention includes the individual stereoisomers, and the mixtures thereof. The individual isomers may be prepared or isolated by methods known to those skilled in the art of synthetic organic chemistry.

In parenteral administration of the novel compounds and compositions of the invention the compounds may be formulated in aqueous injection solutions which may contain antioxidants, buffers, bacteriostats, and other conventional pharmaceutical excipients. Extemporaneous injection solutions may be prepared from sterile pills, granules or tablets which may contain diluents, dispersing and surface active agents, binders, and lubricants as well as other pharmaceutical processing aids.

In the case of oral administration, fine powder or granules of the compounds may be formulated with diluents and dispersing and surface active agents, and may be prepared in a draft in water or in a syrup, in capsules or cachets in the dry state or in a non-aqueous suspension, where a suspending agent may be included. The compounds may also be administered in a tablet form along with optional binders and lubricants, or in a suspension in water or syrup or an oil or in a water/oil emulsion and may include flavoring, preserving, suspending, thickening and emulsifying agents. The granules or tablets for oral administration may be coated and other pharmaceutically acceptable agents and formulations may be utilized by those skilled in the art of pharmacy.

The following examples are illustrative of preferred embodiments of methods of preparation and compounds of the invention and are not to be construed as limiting the invention thereto. All percentages are based on weight of the final formulation unless otherwise indicated and the weight of all formulations totals 100% by weight.

The novel compounds of the invention may readily be prepared by the following synthetic routes:

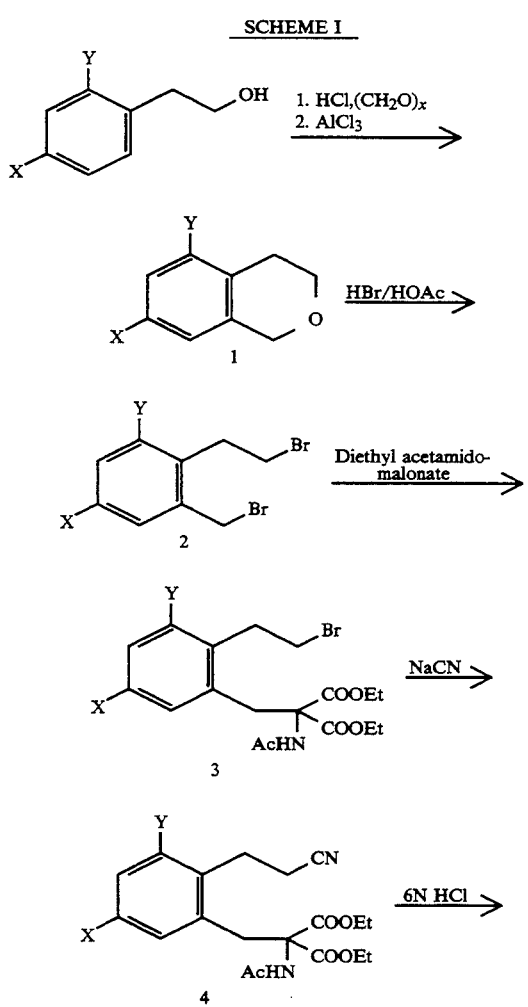

-continued
SCHEME I

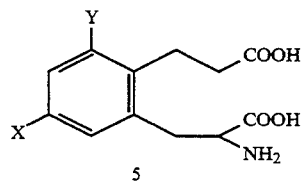

In the case of the sulfonic acid-substituted compounds, the sulfonates were prepared from the corresponding bromo intermediates by the following sequence. Bromo compounds 6 were prepared as described in the other schemes.

SCHEME II

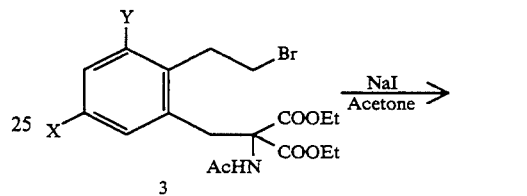

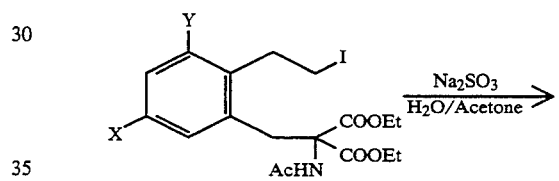

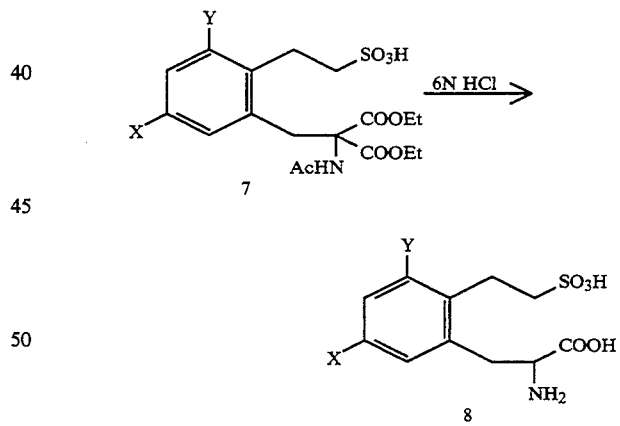

In the case of the 3,5-dimethyl compounds, the phenethyl alcohol was prepared from the commercially available benzoic acid by the following classical series of reactions:

SCHEME III

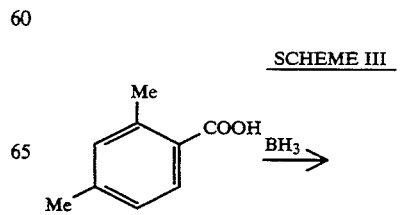

-continued
SCHEME III
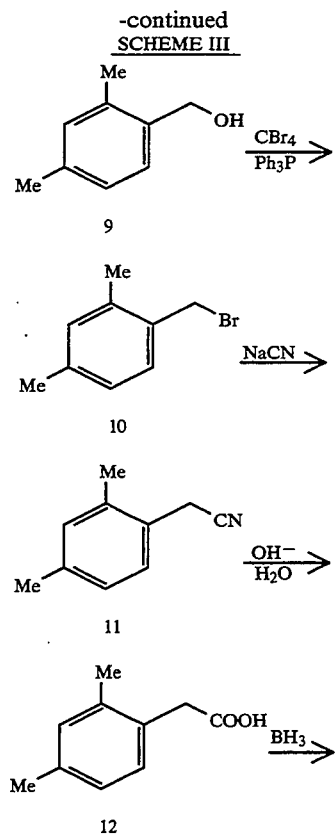
The 4,5-disubstituted compounds were prepared from the corresponding phthalic anhydrides by the following route:
SCHEME IV
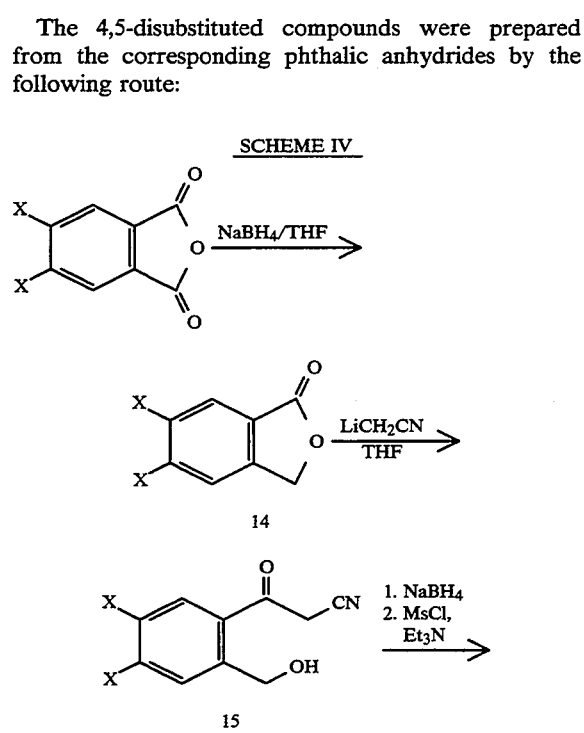
-continued
SCHEME IV
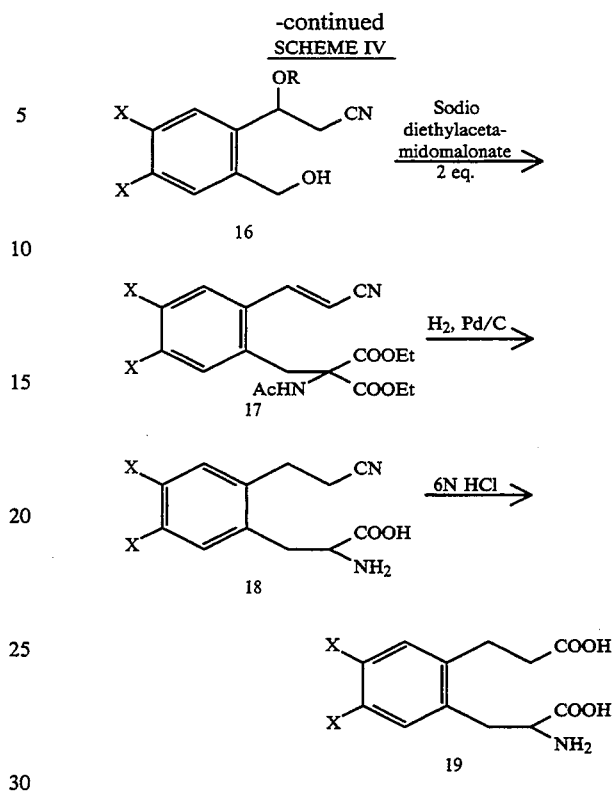
Compounds in which m=3 may be prepared by the route shown in Scheme V:
SCHEME V
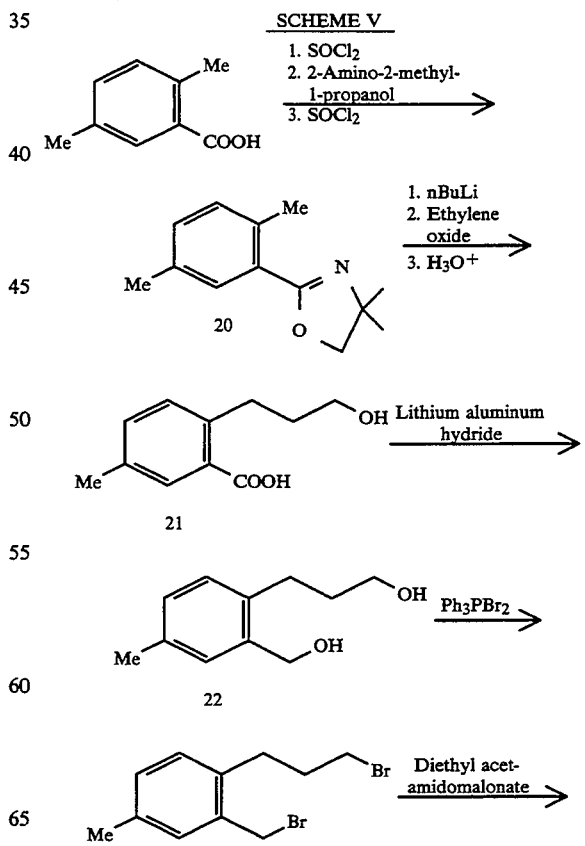

-continued
SCHEME V

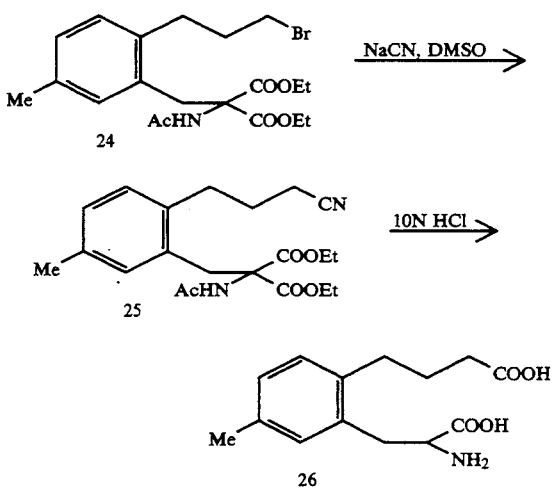

Tetrazole compounds 27 were prepared from cyanomalonates 4 via dipolar cycloaddition using tributyltin azide as the 1,3-dipole, as depicted in Scheme VI:

SCHEME VI

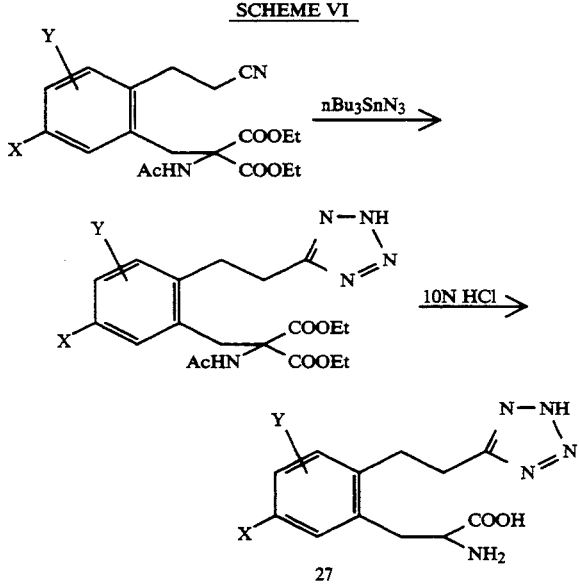

In the following procedure, Y=H unless specifically noted otherwise.

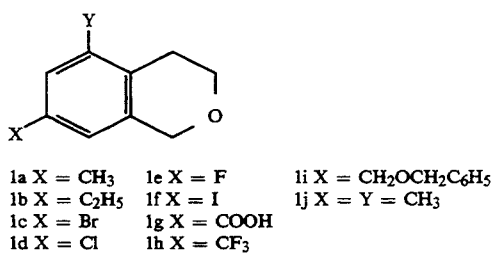

| | | |
|---|---|---|
| 1a X = CH3 | 1e X = F | 1i X = CH2OCH2C6H5 |
| 1b X = C2H5 | 1f X = I | 1j X = Y = CH3 |
| 1c X = Br | 1g X = COOH | |
| 1d X = Cl | 1h X = CF3 | |

General Procedure for the Synthesis of 7-Substituted Isochromans 1. Runs A–E.

A mixture of the substituted phenethyl alcohol (1eq), methoxyethoxymethyl (MEM) chloride (1.5 eq) and N,N-diisopropylethylamine (1.5 eq) in dry methylene chloride (2 ml per mmol of phenethyl alcohol) was stirred at room temperature (about 24 ° C.) for 2 hours. The reaction mixture was washed with 1N HCl (2×75 ml), dried (MgSO4) and evaporated. A solution of the crude MEM acetal in dry methylene chloride (1 ml per mmol) was added to a cooled (0° C.) solution of titanium tetrachloride (2 eq) in methylene chloride (10 ml per mmol of acetal). This mixture was stirred at 0° C. for 2 hours and then quenched by the successive addition of methanol (0.2 ml per mmol of acetal) and 3N HCl saturated with sodium chloride (50 ml). The organic phase was dried (MgSO4). The product was purified by column chromatography (silica gel, 5% ethyl acetate-hexane) to give the 7-substituted isochromans.

A) 7-Methylisochroman (1a, X=CH3, 89% yield). 1H NMR (CDCl3):δ2.27 (s, 3H); 2.77 (t,2H); 3.92 (t, 2H); 4.70 (s, 2H); 6.95 (m, 3H). IR (neat): 1244, 1128 cm$^{-1}$.

B) 7-Ethylisochroman (1b, X=C2H5, 93% yield). 1H NMR (CDCl3):δ1.1 (t, 3H); 2.4–2.8 (m, 4H); 3.8 (t, 2H); 6.6–6.9 (m, 3H). IR (neat): 3000, 1223, 1105 cm$^{-1}$.

C) 7-Bromoisochroman (1c, X=Br, 68% yield). 1H NMR (CDCl3):δ2.75 (m, 2H); 3.92 (t, 2H); 4.69 (s, 2H); 6.94–7.39 (m, 3H), IR (neat): 2850, 1600, 1480, 1190, 1110, 815 cm$^{-1}$.

D) 7-Chloroisochroman (1d, X=Cl, 65% yield). 1H NMR (CDCl3):δ2.89 (t, 2H); 3.95 (t,2H); 4.65 (s, 2H); 6.97–7.14 (m, 3H). IR (neat): 2931, 2852, 2486, 1424, 1293, 1106 cm$^{-1}$.

E) 7-Fluoroisochroman (1e, X=F, 69% yield). $^1$H NMR (CDCl3): δ2.85 (t, 2H); 3.98 (t, 2H); 4.75 (s, 2H); 6.76 (m, 1H); 6.95 (m, 1H); 7.23 (m, 1H). IR (neat): 2931, 2859, 1502, 1432, 1260, 1223, 1113, 1095, 949 cm$^{-1}$.

Synthesis of 7-Iodoisochroman (1f; X=I; 51%)

A solution of 7-bromoisochroman (6.6 g; 30.98 mmmol) in THF (100 ml) was cooled to −78° C. and treated with 2.1 eq of tert-butyllithium (40 ml of a 1.7M solution). After stirring the dark red solution for one minute, iodine (8.64 g; 34.08 mmol) was added as a tetrahydrofuran (THF) solution (50 ml). The reaction mixture was stirred for 30 minutes at −78° C. and one hour at room temperature (about 24° C.). The reaction was quenched with saturated aqueous ammonium chloride, and the organic phase was washed with aqueous sodium thiosulfate and brine, dried, and freed of solvent. The crude product was recrystallized from hexane to provide the pure 5-iodoisochroman as a white crystalline solid, mp=54°–56° C. (4.1 g; 51%). 1H NMR (CDCl3): 2.79 (t, 2H); 3.94 (t,2H); 4.70 (s,2H); 6.85 (d, 1H); 7.32 (s, 1H); 7.46 (d, 1H). IR (nujol): 2931, 2852, 1550, 1252, 1190, 1105, 1005, 987 cm$^{-1}$.

Synthesis of 7-Carboxyisochroman (1 g)

A solution of 7-bromoisochroman (7 g; 32.86 mmol) in THF (100 ml) was cooled to −78° C. and treated with 40.6 ml of a 1.7M solution of tert-butyllithium in pentane (69 mmol; 2.1 eq). Powdered dry ice (excess) was added to the red anion solution within 45 seconds. The reaction mixture was stirred for 30 minutes at −78° C. and 1 hour at room temperature. The reaction was quenched with 60 ml of 1N HCl and extracted with 3×70 ml of ether. The ether layers were combined and washed with brine until the pH was neutral, dried with MgSO4, and concentrated in vacuo. The product was obtained as a white solid, mp 140°–142° C. (5.7 g; 82%). 1H NMR (CDCl3): δ2.95 (t, 2H); 4.03 (t, 2H); 4.83 (s, 2H); 7.24 (t, 1H); 7.89 (s, 1H); 7.92 (d, 1H). IR (KBr): 2954, 2561, 1684, 1427, 1293, 1108 cm$^{-1}$.

Synthesis of 7-Trifluoromethylisochroman (1b)

Diethylaminosulfur trifluoride (2.0 g; 12.5 mmol) was added dropwise to a solution of 7-carboxyisochroman (1.0 g; 4.9 mmol) in 8 ml of diethyleneglycol dimethyl ether at 0° C. Sodium fluoride (300 mg) was then added and the reaction mixture was stirred at 80° C., for 20 hours. It was quenched with 10 ml of 20% aqueous ammonium chloride and 5 ml of water. The mixture was extracted with 4×100 ml of ether; the ether fractions were washed with water and then brine until the pH was neutral. Evaporation of the solvent gave a brown oil, which was purified on a silica gel column to obtain the product as a yellowish oil. 1H NMR (CDCl$_3$): δ2.94 (t, 2H); 3.99 (t, 2H); 4.80 (s, 2H); 7.26 (d, 1H); 7,83 (d, 1H). IR (CDCl$_3$): 2949, 2872, 1810, 1614, 1257, 1100, 1046, 910, 745 cm$^{-1}$.

Synthesis of 2,4 -dimethylbenzyl alcohol (9): 2,4 dimethylbenzoic acid (10 g; 66.6 mmol) in dry tetrahydrofuran (250 ml) was cooled to 0° C. and treated with a solution of diborane in tetrahydrofuran (135 ml of a 1.0M solution). The reaction mixture was stirred overnight before quenching with 1N HCl and extraction of the product into ethyl acetate. The organic phase was dried (MgSO$_4$) and freed of solvent. The crude product was filtered through a plug of silica, eluting with 10% ethyl acetate in hexane, to obtain 8.62 g (95%) of the alcohol as a clear oil. 1H NMR (CDCl$_3$): δ2.30, 2.32 (s, 6H total); 4.63 (d, 2H); 6.99 (m, 2H); 7.23 (d, 1H). IR (neat): 3338, 2921, 1504, 1453, 1378, 1240, 1039, 1005, 820 cm$^{-1}$.

2,4-Dimethylbenzyl bromide (10):

A solution of benzyl alcohol 9 (18.4 g; 135 mmol) and carbon tetrabromide (55.96 g; 169 mmol) in methylene chloride (220 ml) was cooled to 0° C. and treated in dropwise fashion with triphenylphosphine (44.33 g; 169 mmol) in 100 ml of methylene chloride. After the addition was complete the mixture was stirred overnight at room temperature. It was poured into ice-water and partitioned between methylene chloride and water. The organic phase was dried (MgSO$_4$) and concentrated in vacuo. Chromatography of the residue, eluting with 10% ethyl acetate in hexane, gave 26 g (99%) of the product as a yellow liquid. 1HNMR (CDCl$_3$): δ2.31, 2.38 (s, 3H each); 4.51 (s, 2H); 6.99 (m, 2H); 7.18 (d, 1H). IR (neat): 3013, 2972, 2921, 1617, 1507, 1450, 1262, 823 cm$^{-1}$.

2,4-Dimethylbenzyl cyanide (12):

A mixture of bromide 7 (25. g; 130 mmol) and sodium cyanide (7.97 g; 160 mmol) in DMSO (100 ml) was heated to 80° C. for 4 hours. After cooling, the reaction mixture was partitioned between water and ethyl acetate, and the organic phase was washed with brine, dried (MgSO$_4$) and concentrated in vacuo. Purification of the crude product on a silica gel column, eluting with 20% ethyl acetate in hexane, gave 13.8 g (73%) of the product as a brownish oil. 1H NMR (CDCl$_3$): δ2.24, 2.30 (s, 3H each); 3.61 (s, 2H); 7.03 (m, 2H); 7.23 (d, 1H). IR (neat): 2924, 2250, 1504, 1450, 1416, 1381, 1036, 820 cm$^{-1}$.

2,4-Dimethylphenylacetic acid (12):

Nitrile 8 (13.8 g) was refluxed vigorously for 5 days in a mixture of ethanol (80 ml), water (40 ml) and potassium hydroxide (20 g). The ethanol was removed in vacuo and the residue was acidified with concentrated HCl to pH 1. The resulting white precipitate was collected via vacuum filtration, washed with cold water, and dried in a vacuum desiccator. The carboxylic acid was obtained as an off-white solid (14 g; 90%). H NMR (CDCl$_3$): δ2.25, 2.29 (s, 3H each); 3.62 (s, 2H); 6.98–7.01 (m, 3H). IR (nujol): 2921, 1710, 1550,k 1412, 1247, 770 cm$^{-1}$.

2,4-Dimethylphenethyl alcohol (13):

A solution of carboxylic acid 9 (3.40 g; 17.87 mmol) in THF (100 ml) was cooled to 0° C. and treated with 35 ml of a 1.0M solution of borane in THF. After stirring this mixture overnight it was quenched with 1N HCl and the product was extracted into ethyl acetate. The ethyl acetate layer was washed with water, dried (MgSO$_4$) and freed of solvent. The crude product was filtered through a plug of silica gel eluting with 20% ethyl acetate in hexane to obtain 2.75 g (quantitative yield) of the product as a clear light oil. 1H NMR (CDCl$_3$): δ2.25, 2.28 (s, 3H each); 2.88 (t, 2H); 3.78 (t, 2H); 6.97–7.07 (m, 3H). IR (neat): 3340, 2947, 1504, 1448, 1265, 1044 cm$^{-1}$.

5,7-Dimethylisochroman (1j):

A mixture of alcohol 10 (2.75 g; 18 mmol), MEM chloride (3.36 g; 27 mmol) and N,N-diisopropylethylamine (3.49 g; 27 mmol) in methylene chloride (20 ml) was stirred together for 2 hours. The reaction mixture was partitioned between 1N HCl and methylene chloride; the organic phase was washed with brine, dried (MgSO$_4$) and the solvent evaporated.

The crude acetal was dissolved in 20 ml of dry methylene chloride and added via dropping funnel to a stirred, cooled (0° C.) solution of titanium tetrachloride (17 mmol) in 85 ml of methylene chloride. After stirring at 0° C. for 2 hours the reaction was quenched by the successive addition of methanol (5 ml) and 1N HCl (100 ml). The layers were separated and the organic phase was washed with brine, dried (MgSO$_4$) and freed of solvent. The crude material was recrystallized from hexane to obtain 1.2 g (44%) of the isochroman. 1H NMR (CDCl$_3$): δ2.19, 2.27 (s, 3H each); 2.66 (t, 2H); 3.98 (t, 2H); 4.72 (s, 2H); 6.65 (s, 1H); 6.87 (s, 1H).

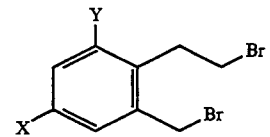

| 2a X = CH$_3$ | 2d X = Cl | 2g X = CH$_2$OCH$_2$C$_6$H$_5$ |
| 2b X = C$_2$H$_5$ | 2e X = F | 2h X = CF$_3$ |
| 2c X = Br | 2f X = I | 2i X = Y = CH$_3$ |

General Procedure for the Synthesis of 5-Substituted 2-(2-Bromoethyl) Benzyl Bromides 2. Runs A–I.

A solution of 7-substituted isochroman 1 and 30% HBr in acetic acid (1 ml/4 mmol) was heated in a sealed tube at 100° C. for 16 hours. After cooling to room temperature, the reaction mixture was poured into water. The product was extracted into ether and the organic phase was washed with brine, dried (MgSO$_4$) and freed of solvent. Chromatography of the residue on silica gel with 5% ethyl acetate-hexane furnished dibromide 2.

A) 2-(2-Bromoethyl)-5-methylbenzyl bromide (2a, X=CH$_3$, 89% yield). 1H NMR (CDCl$_3$): δ2.31 (s, 3H); 3.25 (t, 2H); 3.61 (t, 2H); 4.52 (s, 2H); 7.18 (m, 3H).

B) 2-(2-Bromoethyl)-5-ethylbenzyl bromide (2b, X=C$_2$H$_5$, 92% yield). 1H NMR (CDCl$_3$): δ1.2 (t, 3H); 2.5 (q, 2H); 3.2 (m, 2H); 3.5 (m, 2H); 4.5 (s, 7.2 (m, 3H).

C) 2-(2-Bromoethyl)-5-bromobenzyl bromide (2c, X=Br, 84% yield). 1H NMR (CDCl₃): δ3.24 (t, 2H); 3.61 (t, 2H); 4.47 (s, 2H); 7.08–7.50 (m, 3H). IR (nujol): 3010, 2350, 1590, 1480, 1260, 1225, 1090, 980 cm⁻¹. Mp=66°–69° C.

D) 2-(2-Bromoethyl)-5-chlorobenzyl bromide (2d, X=Cl, 92% yield). 1H NMR (CDCl₃): δ3.26 (t, 2H); 3.60 (t, 2H); 4.47 (s, 2H); 7.16 (d, 1H); 7.26 (dd, 1H); 7.34 (d, 1H).

E) 2-(2-Bromoethyl)-5-fluorobenzyl bromide (2e, X=F, 80% yield). 1H NMR (CDCl₃): δ3.26 (t, 2H); 3.61 (t, 2H); 4.49 (s, 2H); 6.97–7.26 (m, 3H).

F) 2-(2-Bromoethyl)-5-iodobenzyl bromide (2f; X=I, 81% yield). 1H NMR (CDCl₃): δ3.24 (t, 2H); 3.63 (t, 2H); 4.45 (s, 2H); 6.96 (d, 1H); 7.63 (d, 1H); 7.69 (d, 1H).

G) 2-(2-Bromoethyl)-5-benzyloxymethylbenzyl bromide (2 g; X=CH₂OCH₂C₆H₅, 98% yield). 1H NMR (CDCl₃): δ3.28 (t, 2H); 3.65 (t, 2H); 4.44 (s, 2H); 4.49 (s, 2H); 4.52 (s, 2H); 7.20–7.38 (m, 8H).

I) 2-(2-Bromoethyl)-3,5-dimethylbenzyl bromide (2i; X=Y=CH₃, 95% yield). ¹H NMR (CDCl₃): δ2.27,2.32 (s, 3H each); 3.28 (t, 2H); 3.58 (t, 2H); 4.53 (s, 2H); 6.97 (s, 1H); 7.02 (s, 1H).

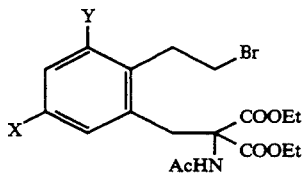

3a X = CH₃    3d X = Cl    3g X = CH₂OCH₂C₆H₅
3b X = C₂H₅   3e X = F     3h X = CF₃
3c X = Br     3f X = I     3i X = Y = CH₃

General Procedure for the Synthesis of Bromomalonates 3. Runs A–I.

To a cooled (10° C.) solution of tetrabutylammonium hydrogen sulfate (50 mmol) in 10% aqueous sodium hydroxide (2.5 equivalents of sodium hydroxide) was added methylene chloride (50 ml) followed by a solution of dibromide 2 (50 mmol) and diethylacetamidomalonate (55 mmol) in methylene chloride (50 ml). After stirring this mixture for 2 hours it was diluted with methylene chloride (200 ml), transferred to a separatory funnel, and the organic phase was washed several times with water and brine, dried (MgSO4) and freed of solvent. Purification by silica gel chromatography (30% ethyl acetate in hexane) afforded the bromomalonates.

A) Ethyl 3-[(2-bromoethyl-5-methyl)phenyl]-2-carboethoxy-2-acetamidopropanoate (3a; X=CH₃; 92% yield). ¹H NMR (CDCl₃): δ1.30 (t, 6H); 2.01 (s, 3H); 2.26 (s, 3H); 3.04 (t, 2H); 3.44 (t,2H); 3.66 (s, 2H); 4.27 (m, 4H); 6.56 (s, 1H); 6.79 (s, 1H); 7.04 (m, 2H). IR(CDCl₃): 1742, 1669cm−1.

B) Ethyl 3-[(2-bromoethyl-5-ethyl)phenyl]-2-carboethoxy-2-acetamidopropanoate (3b; X=C₂H₅; 90% yield). ¹H NMR (CDCl₃): δ1.20 (t, 3H); 1.30 (t, 6H); 2.01 (s, 3H); 2.63 (q, 2H); 3.02 (t,2H); 3.43 (t, 2H); 3.72 (s, 2H); 4.30 (m, 4H); 6.54 (s, 1H; 6.80–7.23 (m, 3H). IR (neat): 1743, 1668 cm−1.

C) Ethyl 3-[(2-bromoethyl-5-bromo) phenyl]-2-carboethoxy-2-acetamidopropanoate (3c; X=Br; 72% yield) . ¹H NMR (CDCl₃): δ1.30 (m, 6H); 2.04 (s, 3H); 3.03 (dd, 2H); 3.43 (dd, 2H); 3.68 (s,2H); 4.22–4.34 (m, 4H); 6.57 (br s, 1H); 7.04–7.35 (m, 3H). IR (nujol): 3296, 1748, 1645, 1519, 1308, 1277, 1221, 1190cm−1. Mp=102°–103° C.

D) Ethyl 3-[(2-bromoethyl-5-chloro) phenyl]-2-carboethoxy-2-acetamidopropanoate (3d, X=Cl, 77% yield). ¹H NMR (CDCl₃): δ1.27 (t, 6H); 2.03 (s, 3H); 2.98 (t, 2H); 3.58 (t, 2H); 3.69 (s, 2H); 4.21–4.30 (m, 4H); 6.62 (br s, 1H); 6.98 (s, 1H); 7.13–7.17 (m, 2H). IR (nujol): 3292, 2905, 1748, 1646, 1519, 1460, 1376, 1309, 1196, 1054, 1021 cm−1.

E) Ethyl 3-[(2-bromoethyl-5-fluoro)phenyl]-2-carboethoxy-2-acetamidopropanoate (3e, x=F, 84% yield). ¹H NMR (CDCl₃): δ1.27 (t, 6H); 2.03 (s, 3H); 2.99 (t, 2H); 3.58 (t, 2H); 3.70 (t, 2H); 4.20–4.33 (m, 4H); 6.60 (br s, 1H); 6.73 (dd, 1H); 6.94 (m, 1H); 7.15 (t, 1H). IR (CHCl3): 3019, 1738, 1680, 1501, 1219 cm−1.

F) Ethyl 3-[(2-bromoethyl-5-iodo)phenyl]-2-carboethoxy-2-acetamidopropanoate (3f, X=I, 65%). ¹H NMR (CDCl₃): δ1.31 (t, 6H); 2.04 (s, 3H)(); 3.03 (t, 2H; 3.44 (t, 2H); 3.65 (s, 2H); 4.32(m, 4H); 6.56 (br s, 1H); 6.94 (d, 1H); 7.34 (s, 1H); 7.53 (dd, 1H). IR (CHCl3): 3019, 1738, 1680, 1497, 1214 cm−1.

G) Ethyl 3-[(2-bromoethyl-5-benzyloxymethyl)phenyl]-2-carboethoxy-2-acetamidopropanoate (3 g, X=CH₂OCH₂C₆H₅, 35% yield). ¹H NMR (CDCl₃): d 1.24 (m, 6H); 2.05 (s, 3H); 3.06 (t, 2H);3.43 (t, 2H); 3.56 (s, 2H); 3.64 (s, 2H); 4.20 (q, 4H); 6.63 (s, 1H); 6.68 (m, 5H); 6.69 (s, 1H);6.83 (d, 1H); 7.06 (d, 1H). IR (CDCl₃): 3422, 2990, 1743, 1676, 1501, 1295, 1211, 1105, 915, 738 cm−1.

I) Ethyl 3-[(2-bromoethyl-3,5-dimethyl)phenyl]-2-carboethoxy-2-acetamidopropanoate (3i, X=Y=CH₃, 73% yield). ¹H NMR (CDCl₃): δ1.27 (t, 6H); 2.03 (s, 3H); 2.21, 2.28 (s, 3H each); 3.04(t, 2H); 3.26 (t, 2H); 3.66 (s, 2H); 4.22 (q, 4H); 6.51 (s, 1H); 6.64 (s, 1H); 6.89 (s, 1H). IR (CDCl₃): 3415, 2983, 1738, 1680, 1494, 1280, 1203, 910, 728 cm−1.

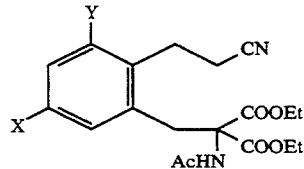

4a: X = F, Y = H
4b: X = Cl, Y = H
4c: X = Y = CH₃

General Procedure for the Synthesis of Cyanomalonates 4. Runs A–D.

Sodium cyanide (12 mmol) was added to a stirred solution of bromo malonate 3 (10 mmol) in dry dimethylsulfoxide (20 ml) and the resulting mixture was heated to 80C for four hours. The reaction mixture was cooled, poured into ice water, and extracted into ethyl acetate. The organic phase was washed with several portions of brine, dried (MgSO4) and freed of solvent. The product was purified on a silica gel column, and eluted with 2:1 hexane/ethyl acetate to obtain nitrites 4 as white solids.

A) Ethyl 3-[(2-Cyanoethyl-5-fluoro)phenyl]-2-carboethoxy-2-acetamidopropanoate (4 a, X=F, Y=H, 72% yield). ¹H NMR (CDCl₃): δ1.21-1.31 (t, 6H); 2.02 (s, 3H); 2.54 (t, 2H); 2.89 (t, 2H); 3.69 (t, 2H); 4.11–4.34 (m, 4H); 6.66 (br, 1H); 6.69 (dd, 1H); 6.73–6.94 (m, 1H); 7.17–7.27 (m, 1H) .

B) Ethyl 3-[(2-Cyanoethyl-5-chloro)phenyl]-2-carboethoxy-2-acetamidopropanoate (4b, X=Cl, Y=H, 64% yield). ¹H NMR (CDCl₃): δ1.26–1.32 (t, 6H); 2.03 (s, 3H); 2.52–2.56 (t, 2H); 2.86–2.91 (t, 2H); 3.67 (s, 2H); 4.22–4.34 (m, 4H); 6.63 (br, 1H); 6.99 (s, 1H); 7.15–7.27 (m, 2H).

C) Ethyl 3-[(2-Cyanoethyl-3,5-dimethyl)phenyl]-2-carboethoxy-2-acetamidopropanoate (4c; X═Y═CH₃, 72% yield). ¹H NMR (CDCl₃): δ1.2–1.32 (t, 6H); 1.97 (s, 3H); 2.22 (s, 3H); 2.29 (s, 3H); 2.96–3.02 (t, 2H); 3.42–3.47 (t, 2H); 3.67 (s, 2H); 4.20–4.30 (m, 4H); 6.52 (br, 1H); 6.65 (s, 1H); 6.89 (s, 1H).

D) Ethyl 3- [(2-Cyanoethyl-5-methyl)phenyl]-2-carboethoxy-2-acetamidopropanoate (4d; X═CH₃, Y═H; 66% yield). ¹H NMR (CDCl₃): δ1.29 (t, 6H); 2.00 (s, 3H); 2.26 (s, 3H); 2.53 (t, 2H); 2.86 (t, 2H); 3.65 (s, 2H); 4.31 (m, 4H); 6.56 (br, 1H); 6.78 (s, 1H); 7.15 (m, 2H). IR (nujol): 3154, 2255, 1795, 1738, 1676, 1471, 1381, 908, 727 cm⁻¹.

Synthesis of Cyanomalonate 18 (Scheme IV)

5,6-Dichlorobenzofuran-1-one (14):

To a stirred suspension of sodium borohydride (0.70 g; 18.5 mmol) in 60 ml of THF, cooled to 0° C., 4,5-dichlorophthalic anhydride (5.0 g; 23.0 mmol) was added portionwise. The resulting mixture was stirred at 0° C. for 15 minutes and room temperature for 1 hour. After cooling back to 0° C., 30 ml of 3N HCl were added slowly and the resulting mixture was heated to 60° C. for 2 hours. After returning to room temperature, the formed white solid was collected via vacuum filtration and dried to furnish 3.8 g (81%) of lactone 14.

Hydroxy cyano ketone 15:

Acetonitrile (10 mmol) was added to a stirred solution of lithium diisopropylamide (11 mmol) in 30 ml of THF at −23° C. After stirring for 30 minutes, lactone (9 mmol) was added as a suspension in THF (30 ml). The reaction mixture was allowed to warm to room temperature and stirred for 2 hours, then quenched by the addition of 50 ml of saturated ammonium chloride. The layers were separated, and the organic phase was washed with brine, dried, and concentrated. Purification of the product on silica gel furnished keto nitrile 15.

Dimesylate 96:

Sodium borohydride (11 mmol) was added in portions to a cooled (0° C.) stirred suspension of ketone (10 mmol) in 7 ml of methanol After stirring for 20 minutes at 0° C., ether (10 ml) was added and the organic phase was washed with 1N HCl (6 ml) and brine (6 ml). The organic layer was dried (MgSO4) and concentrated to provide a colorless oil. This material, together with 22 mmol of triethylamine, was dissolved in 8 ml of methylene chloride and cooled to 0° C., with stirring. Methanesulfonyl chloride, 22 mmol, was added dropwise and the reaction mixture was stirred at 0° C. for 30 minutes. Methanol, 0.5 ml, was added and stirring was continued for an additional 5 minutes. The reaction mixture was concentrated and the crude residue was purified on a silica gel column eluting with ethyl acetate to obtain compound 16.

Vinyl nitrile 17:

Diethyl acetamidomalonate (20 mmol) was added to a stirred suspension of sodium hydride (20 mmol) in THF (20 ml) and stirred for 1 hour at room temperature. Mesylate (10 mmoL) was added as a THF solution and the resulting mixture was heated to 80° C. for 4 days. After cooling to 0° C., it was quenched with 1N HCl (20 ml) and the layers were separated. The organic phase was dried and concentrated to provide 17, which was taken directly to the next step without further purification.

Cyanomalonate 18:

Vinyl nitrile 17 (5 mmol) and 5% palladium on carbon (0.5 mmol) in 10 ml of ethanol were shaken in a Paar hydrogenator under 30 psi of hydrogen for 3 hours. The solution was filtered through Celite and concentrated to provide a crude oil. This was purified through a silica gel column, and eluted with ethyl acetate, to provide 18 as a clear oil which solidified upon standing.

Synthesis of Cyanomalonate 23 (Scheme V)

Oxazoline 20:

A solution of 2,5-dimethylbenzoic acid (133 mmol) in thionyl chloride (70 ml) was refluxed for 3 hours. The solvent was removed in vacuo to provide 22.35 g of crude acid chloride. This was dissolved in methylene chloride (200 ml) and added dropwise to a cooled (0° C.) solution of 2-amino-2-methyl-1-propanol (26 12 g; 278 mmol) in methylene chloride (300 ml). After stirring for 2 hours, the mixture was filtered through Celite to remove the formed precipitate and the solvent was removed in vacuo to deliver 29.07 g of the amide as a white solid. Thionyl chloride, 100 ml, was added dropwise to this crude product in a 500 ml rb flask. The mixture was stirred for 3 hours and then concentrated in vacuo. The solid residue was taken up in methylene chloride and washed several times with 1N NaOH. The organic phase was dried (MgSO4), freed of solvent, and the crude product was purified through a silica gel column, eluting with 10% ethyl acetate/hexane to obtain 19.2 g (72% overall) of 20 as a white solid. ¹H NMR (CDCl3): δ1.37 (s, 6H); 2.30 (s, 3H); 2.50 (s, 3H); 4.04 (s, 2H); 7.09 (d, 1H); 7.58 (d, 1H). IR (nujol): 2905, 2358, 1782, 1640, 1458, 1378, 1347, 1188, 1085 cm⁻¹.

Hydroxy oxazoline 21:

A solution of 20 (8.4 g; 41.38 mmol) in tetrahydrofuran (100 ml) was cooled to 0° C. and treated with nBuLi (18.2 ml of a 2.5M solution; 45.5 mmol). After stirring the red anion solution at 0° C. for 1 hour, ethylene oxide (150 ml of a 1.5M solution) was added and the mixture was stirred overnight. It was quenched by the addition of saturated ammonium chloride (100 ml) followed by 1N HCl (100 ml). The organic phase was concentrated and the crude product was purified on a flash column eluting with 20% ethyl acetate/hexane to obtain 10 g (98%) of as a clear oil. ¹H NMR (CDCl3): δ1.43 (s, 6H); 1.87–1.95 (m, 2H); 2.35 (s, 311); 3.09 (t, 2H); 3.44 (dd, 211); 4.16 (s, 2H); 7.18–7.27 (m, 2H); 7.59 (s, 1H). IR (neat): 3309, 2929, 1646, 1460, 1355, 1311, 1193, 1046 cm⁻¹.

Diol 22:

A solution of hydroxypropyloxazoline 21 (6.31 g; 25.5 mmol) in 3N HCl (100 ml) was heated to 120° C. for 3.5 hours. After cooling the reaction mixture was partitioned between brine and ethyl acetate. The solvent was removed in vacuo and the crude residue was dissolved in 100 ml of tetrahydrofuran and added to a slurry of lithium aluminum hydride in ether (45 mmol of LAH in 115 ml of ether). The reaction mixture was stirred for 2 hours at room temperature and then quenched by the cautious addition of water (40 ml) followed by 1N HCl (120 ml). The reaction mixture was partitioned between ethyl acetate and water; the organic phase was washed with water, dried and freed of solvent. The crude material was chromatographed on a silica gel column, eluting with ethyl acetate to obtain 3.85 g (84%) of 22 as an oil. ¹H NMR (CDCl3): δ1.85 (m,2H); 2.31 (s, 3H); 2.77 (t, 2H); 3.54 (m, 4H); 4.62 (s, 2H); 7.05-7.25 (m, 3H). IR (neat): 3312, 2929, 1450, 1039, 823 cm$^{-1}$.

Dibromide 23:

A solution of dibromotriphenylphosphorane (25 g; 59.22 mmol) in methylene chloride (200 ml) was added to a solution of 22 (3.85 g; 21.36 mmol) in 20 ml of methylene chloride. After stirring at room temperature for 3 hours, the mixture was partitioned between brine and methylene chloride. The organic phase was dried, freed of solvent, and purified on a flash column, eluting with hexane. Compound 23 was obtained as a brown solid (6.06 g; 93%). $^1$H NMR (CDCl$_3$): δ2.18-2.23 (m, 2H); 2.31 (s, 3H); 2.87 (dd, 2H); 3.47 (t, 2H); 4.53 (s, 2H); 7.08-7.25 (m, 3H).

Bromomalonate 24:

A two phase mixture of dibromide 23 (6.05 g; 19.77 mmol), diethyl acetamidomalonate (4.82 g; 21.75 mmol); tetrabutylammonium hydrogen sulfate (7.61 g; 21.75 mmol) in methylene chloride (30 ml) and 10% sodium hydroxide (30 ml) was stirred overnight. The layers were separated and the organic layer was washed several times with brine, dried and freed of solvent. The crude material was purified by passing through a silica gel column, eluting with 1:1 hexane/ethyl acetate. Bromomalonate 24 was obtained as a white solid (6.83 g; 78%). IR (nujol): 3312, 2916, 1743, 1648, 1509, 1458, 1376, 1311, 1270, 1198 cm$^{-1}$.

Cyanomalonate 25:

A mixture of bromomalonate 24 (3.0 g; 6.78 mmol) and sodium cyanide (44 mg; 8.16 mmol) in dimethyl sulfoxide (40 ml) was heated to 90° C. for 5 hours. It was cooled and diluted with 75 ml of ethyl acetate and washed with 5×50 ml of brine. The organic phase was dried, freed of solvent, and purified on a silica gel column, eluting with 1:1 hexane/ethyl acetate to obtain 2.2 g (84%) of nitrile 25 as a white solid. 1H NMR (CDCl$_3$): d 1.28 (t, 611); 1.82 (m, 2H); 2.00 (s, 3H); 2.31 (m, 4H); 2.65 (m, 2H); 3.63 (s, 2H); 4.24 (m, 4H); 6.57 (br, 1H); 6.76 (s, 1H); 7.02 (m, 2H). IR (nujol): 3309, 2913, 2245, 1743, 1650, 1509, 1458, 1375; 1314, 1273, 1200 cm$^{-1}$.

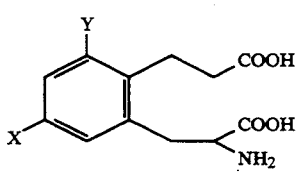

5a: X = F, Y = H
5b: X = Cl, Y = H
5c: X = Y = CH$_3$

General Procedure for the Hydrolysis of Cyanomalonates 4. Preparation of Dicarboxylates 5. Runs A–C.

A solution of cyanomalonate 4 (10 mmol) in 10N HCl (50 ml) was heated to 140° C. for 7 days. The water was removed in vacuo and the brown solid obtained was washed with hexane end ether and dried under vacuum. The residue was dissolved in ethanol (20 ml) and treated with propylons oxide (20 ml). Removal of the solvents furnished an off-white solid which was washed with ether and dried under vacuum.

A) 5-Fluoro-2-(2'-carboxymethyl)phenylalanine (5a, X=F, Y=H, 58% yield). $^1$H NMR (D$_2$O): d 2.23 (t, 2H); 2.68 (m, 4H); 3.27 (t, 1H); 6.74 (d, 111); 6.76 (d, 1H); 7.03 (dd, 1H). IR (nujol): 3194, 2908, 1954, 1687, 1565, 1453, 1280, 1206 cm$^{-1}$. Mp 230° C. (dec). Anal. Calcd. for C12H14NO4F: C, 56.47; H, 5.53; N, 5.49. Found: C, 56.29; H, 5.60; N, 5.41.

B) 5-Chloro-2-(2'-carboxymethyl)phenylalanine (5b, x=Cl, Y=H, 55% yield). $^1$H NMR (D$_2$O): 62.34 (t, 2H); 2.64–2.98 (m, 4H); 3.32 (t, 1H); 7.10 (m, 311). IR (nujol): 3137, 2900, 1687, 1566, 1458, 1278, 1203 cm$^{-1}$. Mp 240° C. (dec). Anal. Calcd. for C12H14NO4Cl 0.25 H2O: C, 52.19; H, 5.29; N, 5.07. Found: C, 52.22; H, 5.30; N, 5.08.

C) 3,5-Dimethyl-2-(2'-carboxyethyl)phenylalanine (5C, X=Y=CH$_3$, 51% yield). $^1$H NMR (D$_2$O): 62.15 (s, 6H); 2.50–3.10 (m, 6H); 3.50 (t, 1H); 6.85 (m, 211). IR (nujol): 2895, 1602, 1460, 1383 cm$^{-1}$. Mp>160° C. (dec). Anal. Calcd. for C14H19NO4— 0.5 H2O: C, 61.30; H, 7.35; N,5.11. Found: C, 61.09; H, 7.56; N, 5.31.

5-Methyl-2-(3'-carboxypropyl) phenylalanine (26, X=CH$_3$, Y=H, m=3). $^1$H NMR (D$_2$O): δ1.55-1.62 (m, 5H); 2.38-2.42 (m, 211); 2.50-2.60 (m, 1H); 2.75-2.91 (m, 1H); 3.22 (t, 1H); 6.82-6.87 (m, 2H); 6.95-7.20 (m, 1H). IR (nujol): 2915, 1715, 1692, 1504, 1460, 1378, 1260cm$^{-1}$. Mp 210° C. (dec). Anal. Calcd. for C141119NO4— 0.25 H2O: C, 62.32; H, 7.28; N,5.19. Found: C, 62.45; H, 7.30; 5.30.

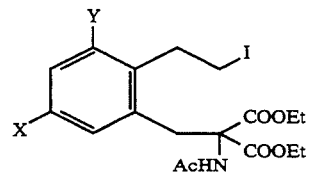

6a: X = CH$_3$, Y = H
6b: X = Y = CH$_3$

General Procedure for the Preparation of Iodomalonates 6. Runs A and B.

A mixture of bromide 3 (10 mmol) and sodium iodide (11 mmol) in acetone (15 ml) was gently warmed (50° C.) for 1 hour. After cooling, the mixture was filtered through Celite and the Celite pad was washed with ether. The filtrate was poured into water and extracted into 350 ml of ethyl acetate. The organic layers were combined, washed with brine, dried, and freed of solvent. The crude residue was purified through a flash column, eluting with 20% ethyl acetate/hexane.

Recrystallization of the product from ether furnished off-white crystalline solids.

A) Ethyl 3[(2-iodoethyl-5-methyl)phenyl]-2-carboethoxy-2-acetamidopropanoate (6a; X=CH$_3$; Y=H; 70% yield). $^1$H NMR (CDCl$_3$): δ1.24 (t, 611); 2.03 (d, 3H); 2.27 (s, 3H); 3.04 (t, 2H); 3.37 (t, 2H); 3.82 (s, 2H); 4.35 (m, 4H); 6.42 (br, 1H); 6.75 (m, 3H).

B) Ethyl 3-[(2-iodoethyl-3,5-dimethyl)phenyl]-2-carboethoxy-2-acetamidopropanoate (6b; X=Y=CH$_3$; 34%). $^1$H NMR (CDCl$_3$): d 1.26 (t, 611); 2.03 (d, 311); (2.35,2.38, s, 6H total); 3.08 (t, 2H); 3.35 (t, 2H); 3.76 (d, 2H); 4.35 (in, 411); 6.55 (br, 1H); 6.66 (d, 1H); 6.86 (d, 1H).

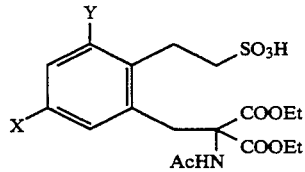

7a: X = CH₃, Y = H
7b: X = Y = CH₃

General Procedure for the Preparation of Sulfonates and Hydrolysis to Sulfonic Acids 8. Runs A and B.

Iodide 6 (3 mmol) was dissolved in 5 ml of acetone and a solution of sodium sulfite (4.5 mmol) in water (5 ml) was added. This mixture was refluxed overnight. After cooling to 0° C., the precipitate which formed was filtered and the filtrate was concentrated to funrnish 7 as yellowish-white solids. This residue was dissolved in 7 ml of 6N HCl and refluxed overnight. The water was removed evaporatively and the brown residue was washed with hexane and ether. It was dissolved in 10 ml of ethanol and treated with an equal volume of propylene oxide. The formed precipitate was filtered and dried under vacuum to obtain final products 8.

A) 5-Methyl-2-(2'-sulfonoethyl)phenylalanine (8a, X=CH₃, Y=H, 45%). ¹H NMR (CDCl₃): δ2.13(s, 3H); 2.89 (m, 5H); 3.18 (dd, 1H); 3.92 (t, 1H); 6.94–7.08 (m, 3H). IR (KBr): 3479, 2942, 1746, 1643, 1540, 1234, 1188, 1041, 810, 784, 609, 537, 478 cm⁻¹. Anal. Calcd. for C12H17NO5S— 1.25 H2O: C, 46.52; H, 6.34; N, 4.52. Found: C, 46.63; H, 5.76; N, 4.53.Mp>235° C. (dec).

B) 3,5-Dimethyl-2-(2'-sulfonoethyl)phenylalanine (8b; X=Y=CH₃, 33%). ¹H NMR (CDCl₃): δ2.13,2.25 (s, 3H each); 2.93 (m, 5H total); 3.14 (m, 1H); 3.88 (t, 1H); 7.02 (m, 2H).

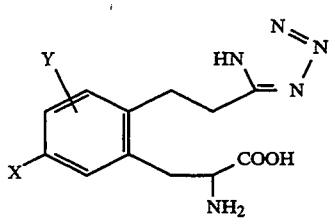

27a: X = CH₃, Y = H
27b: X = Cl, Y = H

Preparation of Tetrazoles 27

5-Methyl-2-(2'-tetrazolylethyl) phenylalanine (27a; X=CH₃, Y=H)

A mixture of cyanomalonate 4d (1.70 g; 4.54 mmol) and tributyltin azide (3.8 g; 11.1 mmol) in toluene (20 ml) was heated to 110° C. for 3 days. The solvent was removed in vacuo and 20 ml of 6N HCl was added to the residue. This mixture was heated to reflux overnight. After cooling, the water was evaporated and the resultant foam was washed with hexane and dried under vacuum. The material was dissolved in a minimal amount of ethanol and treated with an equal volume of propylene oxide. After stirring for 30 minutes the precipitate was collected and dried in a vacuum desiccator to obtain 500 mg of 27a as a tan solid. ¹H NMR (CDCl₃): δ1.29 (t, 6H); 2.00 (s, 3H); 2.26 (s, 3H); 2.53 (t, 2H); 2.86 (t, 2H); 3.65 (s, 2H); 4.31 (m, 4H); 6.56 (br, 1H); 6.78 (s, 1H); 7.15 (m, 2H). Anal. Calcd. for C13H27N5O2: C, 56.71; H, 6.22; N, 22.24. Found: C, 54.47;H, 6.09; N, 22.24.

5-Chloro-2-(2'-tetrazolylethyl)phenylalanine (27b; X=Cl, Y=H)

A mixture of nitrile (1.0 g; 2.53 mmol), tributyltin chloride (0.92 g; 2.78 mmol) and sodium azide (0.19 g; 2.78 mmol) was heated to 110° C. for 70 hours. The toluene was removed in vacuo, and the residue was treated with 15 ml of 10N HCl and refluxed overnight. The water was evaporated to obtain a tan solid, which was washed with ether and ethyl acetate and dried under vacuum. The solids were dissolved in a minimum amount of ethanol and treated with an equal volume of propylene oxide. The precipitate which formed was collected and dried in a vacuum desiccator to obtain 200 mg of tetrazole 27b. ¹H NMR (CDCl₃): δ1.26–1.32 (t, 6H); 2.03 (s, 3H); 2.52–2.56 (t, 2H); 2.86–2.91 (t, 2H); 3.67 (s, 2H); 4.22–4.34 (m, 4H); 6.63 (br, 1H); 6.99 (s, 1H); 7.15–7.27 (m, 2H).

Inhibition of EAA-Induced Currents in Xenopus Oocytes

Defolliculated oocytes obtained from Xenopus laevis females were injected with 30–75 ng of poly (A+) mRNA obtained from 21-day old male Sprague-Dawley rats. Oocytes were placed individually in 100 ml of antibiotic-supplemented modified Barthes solution (MBS, containing in mM: NaCl, 88; KCl, 1.0; NaHCO3, 2.4; HEPES, 10;MgSO4, 0.82; Ca(NO3)2, 0.33) in 96-well sterile plates and cultured for 48–120 hours prior to experimentation. Oocytes were inspected every 24 hours at which time the bathing solution is replaced with fresh MBS.

For electrophysiological studies, oocytes were positioned in a small recording chamber (500 ml) and superfused with antibiotic free MBS supplemented with CaCl2 (final concentration=1.4 mM). Oocytes are impaled with a single glass microelectrode, voltage clamped at −60 to −70 mV, and perfused by gravity feed at a rate of 3–5 m/min at room temperature. Drugs were dissolved in the perfusate (pH adjusted to 7.3–7.4) and perfused for 1–2 min or until the response has reached a plateau, followed by a 4 min perfusion in the absence of drug(s). Antagonists are coperfused with agonists. MBS used in NMDA assays were prepared from "glycine-free", deionized water Potencies to inhibit kainic acid-, AMPA- and NMDA/glycerine-induced currents are determined from concentration-response curves. IC₅₀ values are converted to $K_i$ values for comparison purposes using the Cheng-Prusoff equation.

Inhibition of EAA Receptor Ligand binding

Binding assays for the displacement of [3H]AMPA were performed as described by Murphy et al. (Neurochemical Research. 12: 775–781 [1987]). KA binding assays were performed as described by London et al. (Molecular Pharmacology. 15: 492–505 [1979]; strychnine insensitive glycine binding was evaluated by the method of Snell et al. (European Journal of Pharmacology. 156: 105–110 [1988]).

The results are set forth in Tables I and II.

To illustrate the meaning of the Tables, data from two compounds is briefly discussed below. Compound 26 was found to be reasonably potent in blocking KA induced neurotransmission ($K_i$ of 13 μM). However, the data in Table II show that this compound showed no discernible affinity for NMDA receptors ($K_i$>1000), but good affinity for CNQX labeled non-NMDA receptors ($K_i$=8.4 μM). This data, then, indicates that Compound 26 is a potent antagonist of non-NMDA but not NMDA receptors. Likewise, Compound 5b was found to have a $K_i$ against GLU of >300 μM, versus 51 μM against AMPA; the compound is thus at least six-fold selective for AMPA versus NMDA receptors.

The invention being thus described, it will be obvious that the same may be varied in many ways. Such variations are not to be regarded as a departure from the spirit and scope of the invention and all such modifications are intended to be included within the scope of the claims.

TABLE I

Potencies of example compounds to inhibit KA- and AMPA-induced currents in rat brain mRNA-injected Xenopus oocytes:

| Example | Ki(μM) KA | AMPA |
|---------|-----------|------|
| 5a | >50 | nd |
| 5b | 32 | 96 |
| 5c | 84 | nd |
| 26 | 13.3 | nd |
| 7a | 21 | 51 |

TABLE II

Inhibition of EAA Receptor Ligand Binding Receptor Potency (Ki, μM)

| Example | KA | GLU | AMPA | CNQX | Glycine |
|---------|-----|-------|------|------|---------|
| 5a | 475 | >300 | 168 | nd | 41 |
| 5b | 506 | >300 | 51 | nd | 9.0 |
| 5c | nd | >1000 | nd | nd | 211 |
| 26 | nd | >1000 | nd | 8.4 | 2400 |
| 7a | 469 | >300 | 74 | nd | 74 |

KA - kainic acid
AMPA - α-amino-3-hydroxy-5-methyl-4-isoxazolpropionic acid
GLU - glutamic acid
CNQX - 6-cyano-7-nitroqionoxaline-2,3-dione
nd - not determined

What is claimed is:
1. A compound having the general formula:

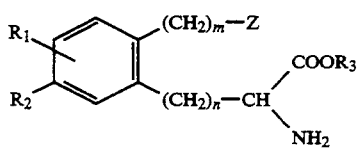

wherein m and n are independently 0, 1, 2, or 3; $R_1$ and $R_2$ are independently selected from the group consisting of hydrogen, halogen, halomethyl, nitro, amino, alkoxy, hydroxyl, hydroxymethyl, C1 to C6 lower alkyl, C7 to C12 higher alkyl, aryl and aralkyl; Z is selected from the group consisting of carboxyl, sulfo and 5-tetrazolyl radical; $R_3$ is selected from the group consisting of hydrogen, and C1 to C6 lower alkyl; and pharmaceutically acceptable salts thereof.

2. The compound according to claim i wherein m is 2.
3. The compound according to claim I wherein m is 3.
4. The compound according to claim i wherein n is 1.
5. The compound according to claim i selected from the group consisting of
5-methyl-2-(3-carboxypropyl)phenylalanine
5-methyl-2-(3-sulfonoethyl)phenylalanine
5-methyl-2-(3-carboxyethyl)phenylalanine
5-methyl-2-(2'-tetrazolylethyl)phenylalanine
3,5-dimethyl-2-(2-carboxypropyl)phenylalanine
3,5-dimethyl-2-(2-sulfonoethyl)phenylalanine
3,5-dimethyl-2-(2-carboxyethyl)phenylalanine
3,5-dimethyl-2-(2'-tetrazolylethyl)phenylalanine
5-chloro-2-(2-carboxypropyl)phenylalanine
5-chloro-2-(2-sulfonoethyl)phenylalanine
5-chloro-2-(2-carboxyethyl)phenylalanine
5-chloro-2-(2'-tetrazolylethyl)phenylalanine
5-methyl-2-(2-carboxypropyl)phenylalanine
5-methyl-2-(2-sulfonoethyl)phenylalanine
5-methyl-2-(2-carboxyethyl)phenylalanine
5-methyl-2-(2'-tetrazolylethyl)phenylalanine
5-fluoro-2-(2-carboxypropyl)phenylalanine
5-fluoro-2-(2-sulfonoethyl)phenylalanine
5-fluoro-2-(2-carboxyethyl)phenylalanine
5-fluoro-2-(2'-tetrazolylethyl)phenylalanine
4,5-dichloro-2-(2-carboxypropyl)phenylalanine
4,5-dichloro-2-(2-sulfonoethyl)phenylalanine
4,5-dichloro-2-(2-carboxyethyl)phenylalanine
4,5-dichloro-2-(2'-tetrazolylethyl)phenylalanine.

6. The compound according to claim 1 being 5-methyl-2-(3-carboxypropyl)phenylalanine.
7. The compound according to claim 1 being 3,5-dimethyl-2-(2-carboxymethyl)phenylalanine.
8. The compound according to claim 1 selected from the group consisting of 5-chloro-2-(2-carboxyethyl) phenylalanine and 5-chloro-2-(2'-tetrazolylethyl) phenylalanine.
9. The compound according to claim 1 being 5-fluor-2-(2-carboxyethyl)phenylalanine.
10. The compound according to claim 1 being 4,5-dichloro-2-(2-carboxymethyl)phenylalanine.
11. The compound according to claim 1 wherein if $R_2$ is hydrogen, $R_1$ is not hydrogen.
12. The compound according to claim 1 wherein if $R_1$ is hydrogen, $R_2$ is not hydrogen.
13. The compound according to claim 1 having greater affinity for KA and AMPA receptors than for other EAA receptors.
14. A compound having the general formula

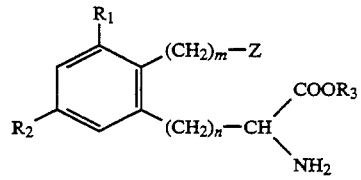

wherein m and n are independently 0, 1, 2, or 3; $R_1$ and $R_2$ are independently selected from the group consisting of hydrogen, halogen, halomethyl, nitro, amino, alkoxy, hydroxyl, hydroxmethyl, C1 to C6 lower alkyl, C7 to C12 higher alkyl, aryl and aralkyl; Z is selected from the group consisting of carboxyl, sulfo and 5-tetrazolyl radical; $R_3$ is selected from the group consisting of hydrogen, and C1 to C6 lower alkyl; and pharmaceutically acceptable salts thereof.

15. A compound having the general formula

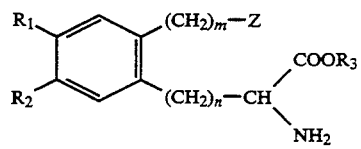

wherein m and n are independently selected from the group consisting of hydrogen, halogen, halomethyl, nitro, amino, alkoxy, hydroxyl, hydroxymethyl, C1 to C6 lower alkyl, C7 to C12 higher alkyl, aryl and aralkyl; Z is selected from the group consisting of carboxyl, sulfo, and 5-tetrazolyl radical; $R_3$ is selected from the group consisting of hydrogen, and C1 to C6 lower alkyl; and pharmaceutically acceptable salts thereof.

16. A pharmaceutical composition which comprises: an effective amount of a compound according to claim 1 together with a pharmaceutically acceptable carrier.

17. A pharmaceutical composition which comprises: an effective amount of a compound according to claim 14 together with a pharmaceutically acceptable carrier.

18. A pharmaceutical composition which comprises: an effective amount of a compound according to claim 15 together with a pharmaceutically acceptable carrier.

19. A method for antagonizing excitatory amino acid kainic acid and AMPA receptors by utilizing a compound having the general formula:

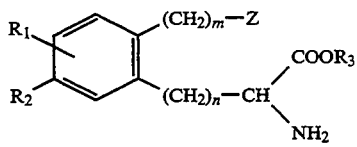

wherein m and n are independently 0, 1, 2, or 3; $R_1$ and $R_2$ are selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl: Z is selected from the group consisting of carboxyl, sulfo and 5-tetrazolyl radical; $R_3$ is selected from the group consisting of hydrogen, and $C_1$ to $C_6$ lower alkyl; and pharmaceutically acceptable salts thereof.

20. The method of claim 19, wherein, when R1 or R2 are hydrogen the other is not hydrogen.

21. The method of claim 19, wherein the excitatory amino acid is selected from the group consisting of
5-methyl-2-(3-carboxypropyl)phenylalanine
5-methyl-2-(3-sulfonoethyl)phenylalanine
5-methyl-2-(3-carboxyethyl)phenylalanine
5-methyl-2-(2'-tetrazolylethyl)phenylalanine
3,5-dimethyl-2-(2-carboxypropyl)phenylalanine
3,5-dimethyl-2-(2-sulfonoethyl)phenylalanine
3,5-dimethyl-2-(2-carboxyethyl)phenylalanine
3,5-dimethyl-2-(2'-tetrazolylethyl)phenylalanine
5-chloro-2-(2-carboxypropyl)phenylalanine
5-chloro-2-(2-sulfonoethyl)phenylalanine
5-chloro-2-(2-carboxyethyl)phenylalanine
5-chloro-2-(2'-tetrazolylethyl)phenylalanine
5-methyl-(2-carboxypropyl)phenylalanine
5-methyl-(2-sulfonoethyl)phenylalanine
5-methyl-(2-carboxyethyl)phenylalanine
5-methyl-(2'-tetrazolylethyl)phenylalanine
5-fluoro-2-(2-carboxypropyl)phenylalanine
5-fluoro-2-(2-sulfonoethyl)phenylalanine
5-fluoro-2-(2-carboxyethyl)phenylalanine
5-fluoro-2-(2'-tetrazolylethyl)phenylalanine
4,5-dichloro-2-(2-carboxypropyl)phenylalanine
4,5-dichloro-2-(2-sulfonoethyl)phenylalanine
4,5-dichloro-2-(2-carboxyethyl)phenylalanine
4,5-dichloro-2-(2'-tetrazolylethyl)phenylalanine.

* * * * *

UNITED STATES PATENT AND TRADEMARK OFFICE
CERTIFICATE OF CORRECTION

PATENT NO. : 5,364,876
DATED : November 15, 1994
INVENTOR(S) : Gregory S. Hamilton It is certified that error appears in the above-indentified patent and that said Letters Patent is hereby corrected as shown below:

Claim 2, column 25, line 54, replace "i" with —1—.

Claim 3, column 25, line 55, replace "I" with —1—.

Claim 4, column 25, line 57, replace "i" with —1—.

Claim 5, column 25, line 58, replace "i" with —1—.

Signed and Sealed this

Seventeenth Day of January, 1995

*Attest:*

BRUCE LEHMAN

*Attesting Officer*  *Commissioner of Patents and Trademarks*